US011904206B2

(12) United States Patent
Nixon

(10) Patent No.: US 11,904,206 B2
(45) Date of Patent: Feb. 20, 2024

(54) INTERACTIVE EXERCISE SYSTEM

(71) Applicant: Raheem J. Nixon, Bridgeport, CT (US)

(72) Inventor: Raheem J. Nixon, Bridgeport, CT (US)

( * ) Notice: Subject to any disclaimer, the term of this patent is extended or adjusted under 35 U.S.C. 154(b) by 916 days.

(21) Appl. No.: 16/704,229

(22) Filed: Dec. 5, 2019

(65) Prior Publication Data
US 2020/0215388 A1 Jul. 9, 2020

Related U.S. Application Data

(60) Provisional application No. 62/790,346, filed on Jan. 9, 2019.

(51) Int. Cl.
*A63B 24/00* (2006.01)
*A61B 5/00* (2006.01)
*A61H 23/04* (2006.01)
*A61F 7/00* (2006.01)
*G16H 20/30* (2018.01)
*A61B 5/11* (2006.01)
*A43B 3/34* (2022.01)

(52) U.S. Cl.
CPC ............ *A63B 24/0059* (2013.01); *A43B 3/34* (2022.01); *A61B 5/0004* (2013.01); *A61B 5/1112* (2013.01); *A61B 5/6807* (2013.01); *A61B 5/749* (2013.01); *A61F 7/00* (2013.01); *A61H 23/04* (2013.01); *A63B 24/0062* (2013.01); *G16H 20/30* (2018.01); *A61B 2562/0219* (2013.01); *A61F 2007/0045* (2013.01); *A61F 2007/0093* (2013.01); *A61H 2201/165* (2013.01); *A61H 2201/5007* (2013.01); *A61H 2205/12* (2013.01)

(58) Field of Classification Search
CPC .......... A61B 5/0004; A61F 2007/0093; A61F 2007/0045; A63B 24/0059; A63B 24/0062
See application file for complete search history.

(56) References Cited

U.S. PATENT DOCUMENTS

| | | |
|---|---|---|
| 5,761,834 A | 6/1998 | Grim |
| 7,204,041 B1 | 4/2007 | Bailey |
| 7,219,449 B1 | 5/2007 | Hoffberg |
| 2007/0000154 A1 | 1/2007 | DiBenedetto |
| 2007/0129907 A1 | 6/2007 | Demon |
| 2014/0165427 A1 | 6/2014 | Molyneux |
| 2015/0182844 A1* | 7/2015 | Jang .......................... A43B 3/34 177/4 |
| 2016/0163182 A1* | 6/2016 | Lyman ...................... G08B 7/06 340/287 |
| 2016/0232550 A1* | 8/2016 | Fletcher ............. G06Q 30/0226 |
| 2018/0055140 A1* | 3/2018 | Antonetti ................. A43B 3/34 |
| 2018/0160975 A1* | 6/2018 | London ................ A61B 5/0205 |

(Continued)

*Primary Examiner* — Pamela M. Bays
*Assistant Examiner* — Amanda L Steinberg
(74) *Attorney, Agent, or Firm* — IP Attorneys Group, LLC; David Chen; Md Alimul Ahsan

(57) ABSTRACT

A system for providing exercise incentives and/or providing massage is disclosed herein. The system includes a pair of shoes to be worn by a user during exercise; a software application downloadable to an electronic device and configured to wirelessly communicate with the pair of shoes; and a server in communication with the software application. In some embodiments, the pair of shoes includes massage pads and cooling/warming elements. The system is primarily useful for providing a monetary incentive to exercise and secondarily useful for providing relief to a user's feet via massage.

18 Claims, 5 Drawing Sheets

(56) References Cited

U.S. PATENT DOCUMENTS

2018/0342106 A1* 11/2018 Rosado ................ G06Q 10/109
2019/0340683 A1* 11/2019 Kundu .................. G06Q 40/02
2021/0145450 A1* 5/2021 Gruentzig ............ A61B 5/6806

* cited by examiner

INTERACTIVE EXERCISE SYSTEM

CROSS-REFERENCE TO RELATED APPLICATION(S)

The present application is related to and claims priority to U.S. Provisional Patent Application No. 62/790,346 filed Jan. 9, 2019, which is incorporated by reference herein in its entirety.

BACKGROUND OF THE INVENTION

The following includes information that may be useful in understanding the present disclosure. It is not an admission that any of the information provided herein is prior art nor material to the presently described or claimed inventions, nor that any publication or document that is specifically or implicitly referenced is prior art.

TECHNICAL FIELD

The present invention relates generally to the field of exercise of existing art and more specifically relates to an exercise incentive system.

RELATED ART

Individuals are always looking for new and unique ways to stay fit and maintain a healthy lifestyle. Traditional exercise routines can be monotonous and boring. Individuals are less likely to stick with a program if they are not enticed and encouraged. Further, exercise can cause stress and discomfort on a users' feet, which can be exacerbated by the footwear the user is wearing. A suitable solution is desired.

U.S. Publication No. 2007/0129907 to Ronald Demon relates to a multifunction shoe with wireless communications capabilities. The described multifunction shoe with wireless communications capabilities includes a controller having a memory, a wireless transceiver in communication with the controller; a sensor system configured to measure shoe parameter data, and a support system for adjusting the support provided by the shoe. The controller may store and transmit user data, shoe parameter data, and performance data via the wireless transceiver. In addition, the controller may store user data of other users and program code received via the wireless transceiver.

SUMMARY OF THE INVENTION

In view of the foregoing disadvantages inherent in the known exercise art, the present disclosure provides a novel interactive exercise system, or "scientific fit program". The general purpose of the present disclosure, which will be described subsequently in greater detail, is to provide an exercise system which may be called "Feetterrestrialnoids" or "Feetterrestrialnōds" to provide exercise incentives and massage.

A system for providing exercise incentives is disclosed herein. The system includes a pair of shoes configured to be worn by a user during exercise, a software application downloadable to an electronic device, and a server in communication with the software application.

At least one shoe of the pair of shoes may include a first controller, a wireless transceiver, and an exercise measuring means, the first controller having a first processor and a first memory. The wireless transceiver and the exercise measuring means may be in communication with the controller. The software application may be configured to wirelessly communicate with the at least one shoe via the electronic device.

The server may include a second processor and a second memory, the second memory storing computer executable instructions that when executed allow the second processor to: receive exercise-data collected by the exercise measuring means; save the exercise-data to a user-profile located in the second memory; generate a monetary amount based on the exercise-data; and credit the monetary amount to the user-profile.

For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and methods of use for the present disclosure, an interactive exercise system, constructed and operative according to the teachings of the present disclosure.

The various embodiments of the present invention will hereinafter be described in conjunction with the appended drawings, wherein like designations denote like elements.

DETAILED DESCRIPTION

As discussed above, embodiments of the present disclosure relate to an interactive exercise system and more particularly to an exercise incentive and massage system as used to improve exercise systems.

Generally disclosed is a system including a pair of shoes including air pressure pods that can be activated by voice to target specific areas on a user's foot. Voice commands may allow users to target specific areas of the foot. In addition, users can activate a heating and/or cooling mechanism in the footwear. The pair of shoes may increase the health properties known from the benefits of a foot massage and in particular acupressure. Acupressure may reduce depression, help headaches, and provide stress relief.

The pair of shoes may be made from quality material that is comfortable and water resistant. The pair of shoes may be charged by cables. In some embodiments, the system may further include a pair of socks including pressure pads therein.

Further, a software application may be provided that is downloadable to an electronic device and is able to communicate with the pair of shoes (or pair of socks in some embodiments) via wireless technology means. The user may earn coins on the application for monetary rewards for exercise. For example, the more a user walks, the more coins/rewards they receive. In some embodiments, the software application may collect exercise data from around the world to generate location safety data. For example, by collecting data from a user walking in a certain area, the system may gain knowledge into that certain area in terms of safety. This data may then be used by the relevant authorities to put appropriate measures in place, such as higher security and police presence in those areas. The system, which may be known as "Scientific Fit Program" may include a "safety" feature. In this example, the software application may include a safety icon, which the user may select to activate the feature. The feature may focus on fighting, emergency, areas, response ("FEAR"). The system may collect data and track information such as areas of high danger, firearm ownership, gun safety, safe travel areas, etc. and the user may access this information via the software application.

In some embodiments, the pair of shoes may be sold with a smart shoe box. The smart shoe box may be a drone kit that is assembled to create or transform into a drone. The shoe box may include hover technology, video recording means, wireless communication means, and a voice command device.

Every pair of shoes may be sold with an alien extraterrestrial DNA certificate certification. In some embodiments, the system may utilize nanotechnology. The footwear may be available in a wide variety of sizes, colors, and designs. The exact specifications may vary.

Referring now more specifically to the drawings by numerals of reference, there is shown in FIGS. 1-5, various views of a system 100.

Figure 1:
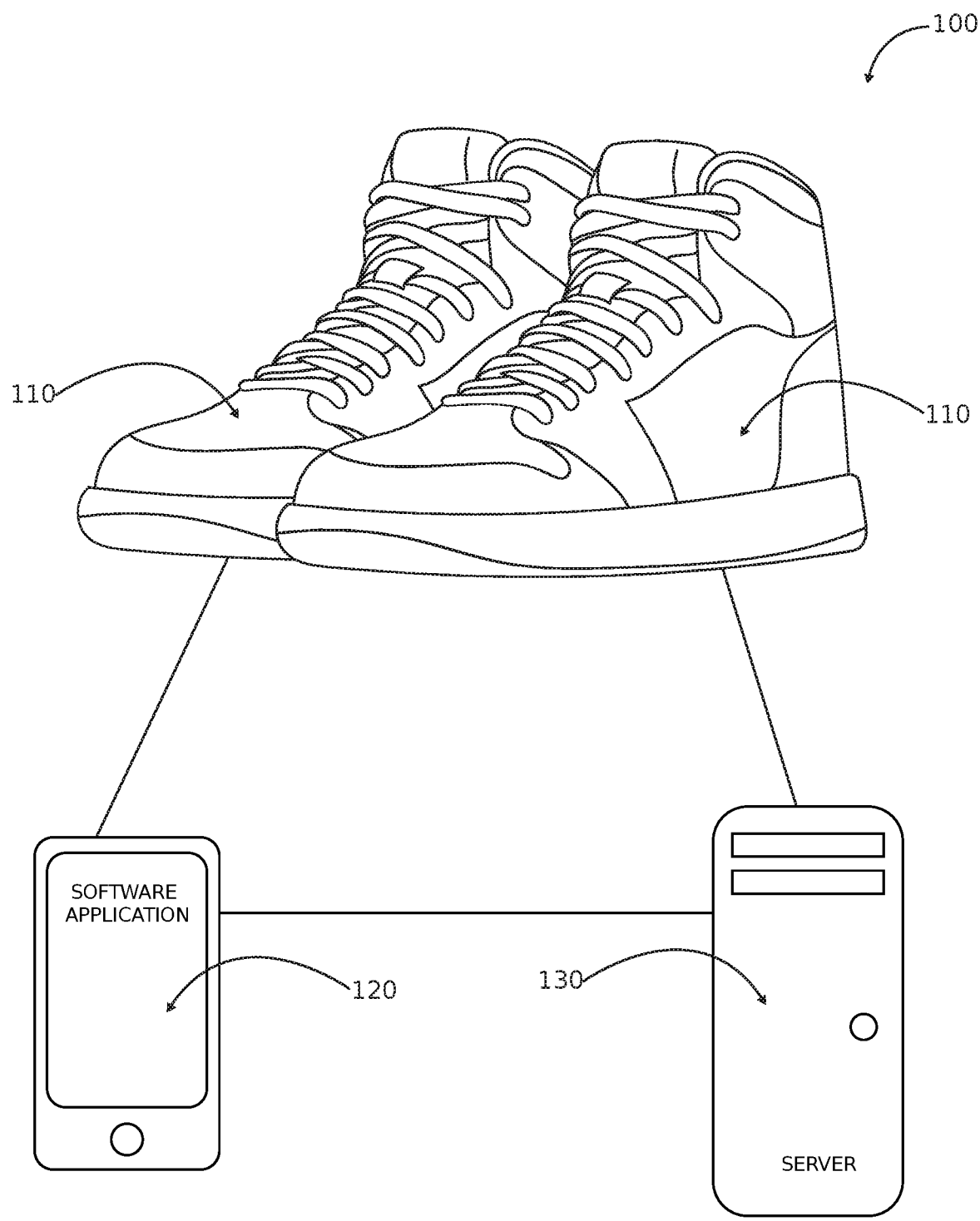
FIG. 1 is a front view of the system during an 'in-use' condition, according to an embodiment of the disclosure.

FIG. 1 shows a system 100 according to an embodiment of the present disclosure. Here, the system 100 may be beneficial to provide massage to feet of a user and provide the user with incentives for exercising. As illustrated, the system 100 may include a pair of shoes 110, a software application 120 and a server 130.

Figure 2:
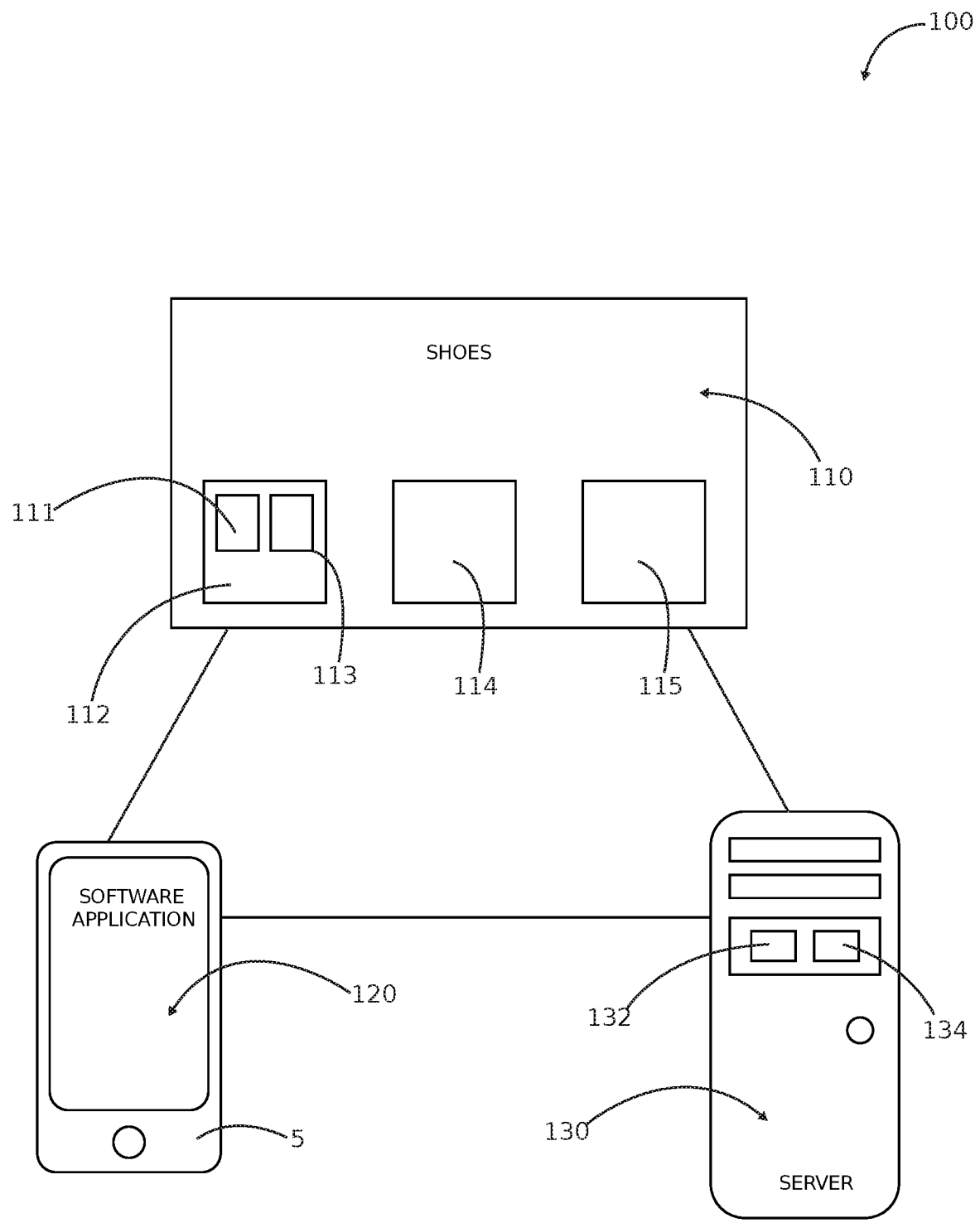
FIG. 2 is a front view of the system of FIG. 1, according to an embodiment of the present disclosure.

FIG. 2 shows the system 100 of FIG. 1, according to an embodiment of the present disclosure. The pair of shoes 110 may be configured to be worn by a user during exercise. At least one shoe of the pair of shoes 110 may include a first controller 112, a wireless transceiver 114, and an exercise measuring means 116. The first controller 112 may have a first processor 111 and a first memory 113, and the wireless transceiver 114 and the exercise measuring means 116 may be in communication with the first controller 112. The software application 120 may be downloadable to an electronic device 5 and configured to wirelessly communicate with the at least one shoe via the electronic device 5. Further, the server 130 may be in communication with the software application 120 and may include a second processor 132 and a second memory 134.

Figure 3:
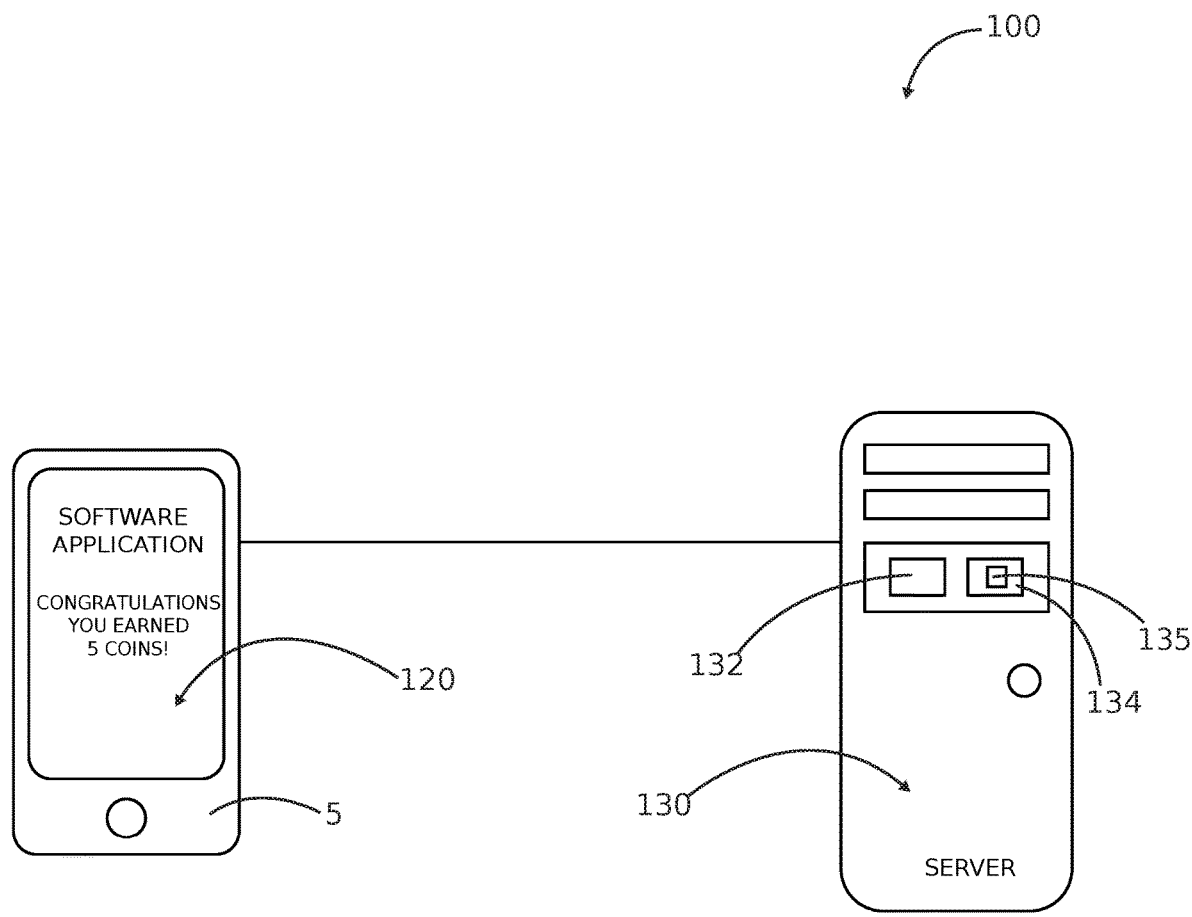
FIG. 3 is a front view of the system of FIG. 1, according to an embodiment of the present disclosure.

FIG. 3 is a front view of the system 100 of FIG. 1, according to an embodiment of the present disclosure. As above, the server 130 may be in communication with the software application 120 and may include the second processor 132 and the second memory 134. The second memory 134 may store computer executable instructions 135 that when executed allow the second processor 132 to receive exercise-data collected by the exercise measuring means 116; save the exercise-data to a user-profile located in the second memory 134; generate a monetary amount based on the exercise-data; and credit the monetary amount to the user-profile. In one embodiment, the monetary amount may be credited as cryptocurrency. In other embodiments, the monetary amount may be credited as rewards for products or services. The products or services may be supplied by participating third party companies. In some embodiments, the monetary amount may be credited as a cash card or a check. In some embodiments, the monetary amount may be credited as donations towards charities, companies, organizations, etc. It should be appreciated that these examples are given as examples only and should not be taken to be the only ways the monetary amount will be credited/utilized.

Figure 4:
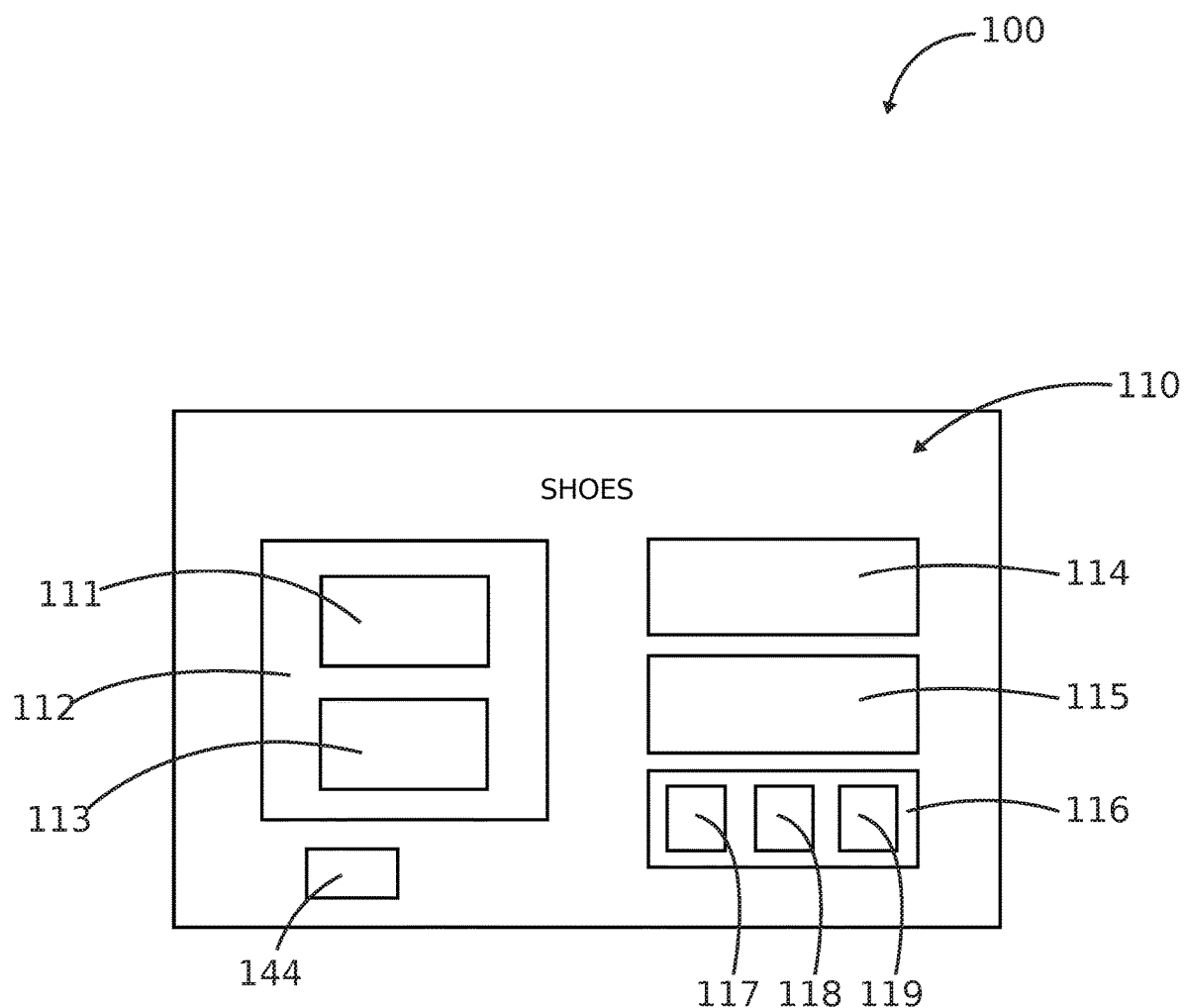
FIG. 4 is a diagram view of the system of FIG. 1, according to an embodiment of the present disclosure.

FIG. 4 is a diagram of the system 100 of FIG. 1, according to an embodiment of the present disclosure. As above, at least one shoe of the pair of shoes 110 may include a first controller 112, a wireless transceiver 114, and an exercise measuring means 116. In one embodiment, the exercise measuring means 116 may include at least one accelerometer 117. Further, in one embodiment, the exercise measuring means 116 may include at least one motion sensor 118. Further still, in one embodiment, the exercise measuring means 116 may include a global positioning system (GPS) receiver 119. It is contemplated that one, some or all of the aforementioned exercise measuring means 116 be utilized, and the list is not exhaustive (other exercise measuring means 116 may be used).

Further, at least one shoe of the pair of shoes 110 may include a voice command device 115. The voice command device 115 may be configured for communication with the software application 120. In addition, each shoe of the pair of shoes 110 may include at least one battery 144. The at least one battery 144 may be rechargeable.

Figure 5:
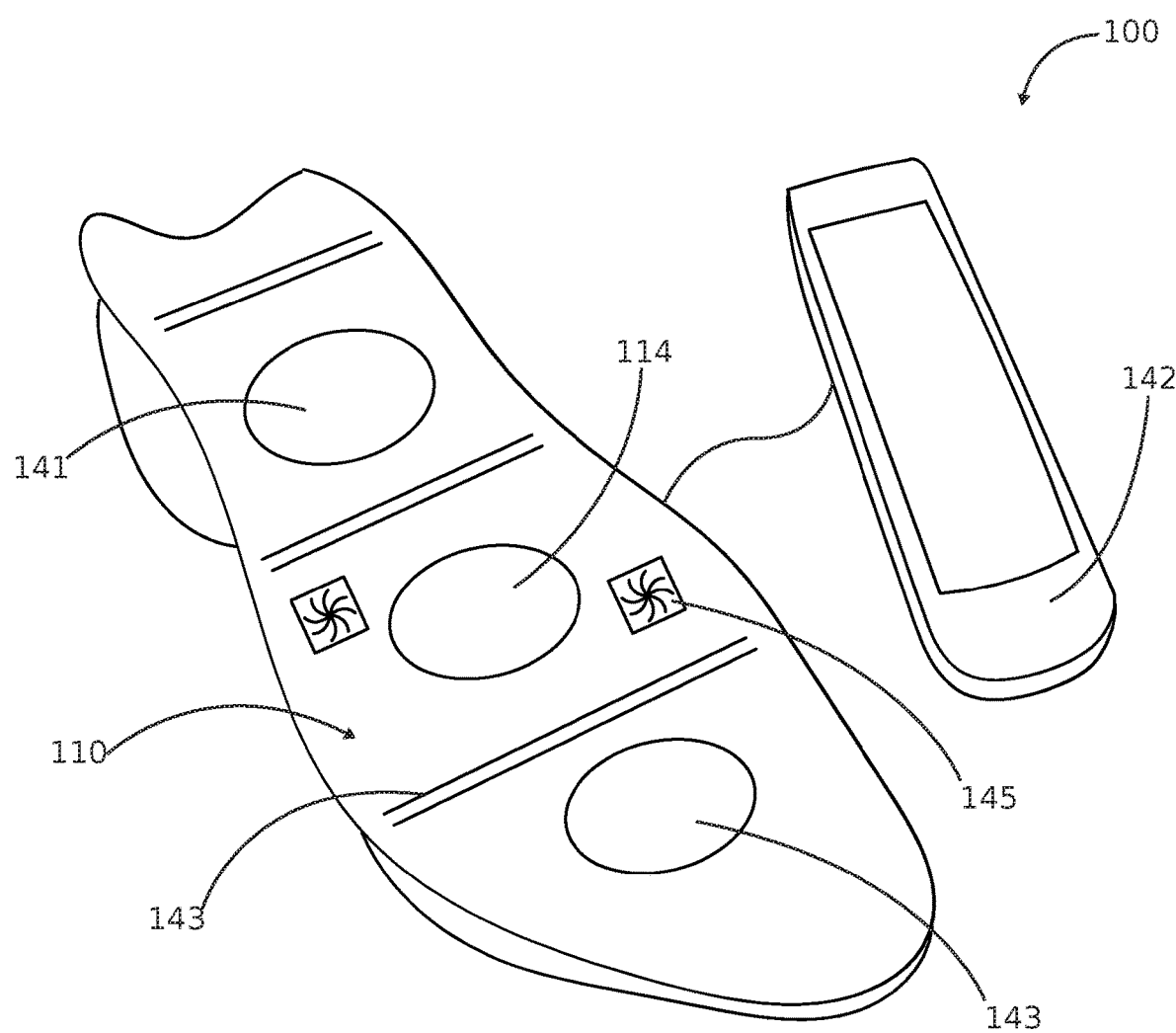
FIG. 5 is a front/side view of the system of FIG. 1, according to an embodiment of the present disclosure.
Figure 5:
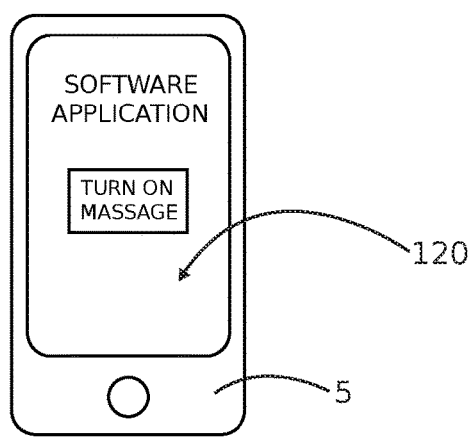

FIG. 5 is a front side view of the system 100 of FIG. 1, according to an embodiment of the present disclosure. In some embodiments, each shoe of the pair of shoes 110 may include a set of massage pads 141 distributed about a base of each shoe; and an air pressure system 142 configured to selectively pump air in and out of each set of massage pads 141. The air pressure system 142 may be integral to both pairs of shoes 110 or at least one; or the air pressure system may be external and connectable to the both pair of shoes 110 or at least one of the pair. Each set of massage pads 141 may be configured to massage each foot of the user in various areas via air pressure selectively pumped in and out of each set of massage pads 141 by the air pressure system 142. Each massage pad in each set of massage pads 141 may be configured for independent activation.

In one embodiment, the air pressure system 142 may be configured for communication with the software application 120. In this embodiment, each massage pad may be selectively activated via a user input on the software application 120. The software application 120 may be configured to receive a user input and communicate with the at least one shoe to selectively activate and deactivate at least one of the air pressure system 142 and the exercise measuring means 116 (FIG. 4) based on the user input. For example, if a user selects to turn on the massage pads 141 on the software application 120, the software application 120 may send a signal to the pair of shoes 110 which may enable the first processor 111 (FIG. 4) to activate the air pressure system 142.

Further, each shoe of the pair of shoes 110 may include a heating and cooling mechanism 143 configured to selectively cool and heat each foot of the user. Preferably, the heating and cooling mechanism 143 may be in communication with the software application 120. In this embodiment, the software application 120 may further be configured to receive the user input and communicate with the at least one shoe to selectively activate and deactivate at least one of the air pressure system 142, the exercise measuring means 116 (FIG. 4) and the heating and cooling mechanism 143 based on the user input.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is new and desired to be protected by Letters Patent is set forth in the appended claims:

1. A system for providing exercise incentives, the system comprising:
    a pair of exercise shoes, at least one of the pair of shoes including a first controller, a wireless transceiver, and an exercise measuring means, the first controller having a first processor and a first memory, and wherein the wireless transceiver and the exercise measuring means are in communication with the first controller;
    a software application downloadable to an electronic device and configured to wirelessly communicate with the at least one shoe via the electronic device; and
    a server in communication with the software application, the server including a second processor and a second memory, the second memory storing computer executable instructions that allow the second processor to
        receive exercise-data collected by the exercise measuring means;
        save the exercise-data to a user-profile located in the second memory;
        generate a monetary amount based on the exercise-data;
        credit the monetary amount as a reward for products or services to the user-profile;
        credit the monetary amount as a donation towards charities, companies, or organizations;
        credit the monetary amount as cryptocurrency; and
        credit the monetary amount as a cash card or a check;
        generate a location safety data based on the exercise data and said location's firearm ownership and gun safety data.

2. The system of claim 1, wherein the exercise measuring means includes at least one accelerometer.

3. The system of claim 1, wherein the exercise measuring means includes at least one motion sensor.

4. The system of claim 1, wherein the exercise measuring means includes a global positioning system (GPS) receiver.

5. The system of claim 1, wherein the at least one shoe of the pair of shoes further includes a voice command device.

6. The system of claim 5, wherein the voice command device is configured for communication with the software application.

7. The system of claim 1, wherein each shoe of the pair of shoes includes a set of massage pads distributed about a base of each shoe.

8. The system of claim 7, wherein at least one shoe of the pair of shoes includes an air pressure system.

9. The system of claim 8, wherein each set of massage pads are configured to massage each foot of the user in various areas via air pressure selectively pumped in and out of each set of massage pads by the air pressure system.

10. The system of claim 1, wherein each shoe of the pair of shoes further includes a heating and cooling mechanism configured to selectively cool and heat each foot of the user.

11. The system of claim 1, wherein one or both of the pair of shoe includes at least one battery.

12. A system for providing exercise incentives and massage, the system comprising:
    a pair of shoes configured to be worn by a user during exercise, each shoe of the pair of shoes including a set of massage pads distributed about a base of each shoe and an air pressure system configured to selectively pump air in and out of each set of massage pads, and wherein at least one shoe of the pair of shoes includes a first controller, a wireless transceiver, and an exercise measuring means, the first controller having a first processor and a first memory, and wherein the wireless transceiver and the exercise measuring means are in communication with the first controller;
    a software application downloadable to an electronic device and configured to wirelessly communicate with the at least one shoe via the electronic device, the software application further being configured to receive a user input and communicate with the at least one shoe to selectively activate and deactivate at least one of the air pressure system and the exercise measuring means based on the user input; and
    a server in communication with the software application, the server including a second processor and a second memory, the second memory storing computer executable instructions that when executed allow the second processor to:
        receive exercise-data collected by the exercise measuring means;
        save the exercise-data to a user-profile located in the second memory;
        generate a monetary amount based on the exercise-data; and
        credit the monetary amount to the user-profile;
        generate a location safety data based on the exercise data and said location's firearm ownership and gun safety data.

13. The system of claim 12, wherein each massage pad in each set of massage pads is configured for independent activation.

14. The system of claim 12, wherein the air pressure system is configured for communication with the software application.

15. The system of claim 14, wherein each massage pad is selectively activated via a user input on the software application.

16. The system of claim 12, wherein the at least one shoe of the pair of shoes further includes a voice command device.

17. The system of claim 16, wherein the voice command device is configured for communication with the software application.

18. The system of claim 12, wherein each shoe of the pair of shoes further includes a heating and cooling mechanism configured to selectively cool and heat each foot of the user.

* * * * *